United States Patent [19]

Flickinger et al.

[11] Patent Number: 5,316,928
[45] Date of Patent: May 31, 1994

[54] DIRECT CALCIUM MAGNESIUM ACETATE PRODUCTION

[75] Inventors: Michael C. Flickinger, Saint Paul; Richard S. Hanson, Wayzata; Frederick J. Schendel, Oakdale; Charles R. Anderson, Apple Valley; Paul R. August, Bloomington, all of Minn.

[73] Assignee: Regents of the University of Minnesota, Minneapolis, Minn.

[21] Appl. No.: 905,170

[22] Filed: Jun. 24, 1992

Related U.S. Application Data

[63] Continuation of Ser. No. 699,997, May 13, 1991, abandoned.

[51] Int. Cl.$^5$ ............................ C12P 7/40; C12P 7/54
[52] U.S. Cl. ............................ 435/136; 435/252.31; 435/832; 435/140; 252/70
[58] Field of Search .................. 252/70; 435/136, 140, 435/252.31, 832

[56] References Cited

U.S. PATENT DOCUMENTS

4,405,717 9/1998 Urbas .................................. 435/140
4,636,467 1/1987 Chynoweth ........................ 435/140

OTHER PUBLICATIONS

D. Wise et al., *Calcium Magnesium Acetate*, D. Wise, Y. Levendis, M. Metghalchi, editors; Elsevier, publishers, Amsterdam, at p. vii (1991).
T. Ghose et al., *Comprehensive Biotechnology*, H. W. Blang, S. Drew, S. Wang (editors); Pergamon Press, vol. 3, 710–729 (1985).
Fukaya et al., *J. Bacteriol.*, 172, 2096 (1990).
Toerien et al., *Water Research*, Pergamon Press, vol. 3, 385–416 (1969).
Grethlein et al., *Proceedings of Corn Utilization Conference II*, Nov. 17–18, 1988.
Tang et al., *Biotechnology and Bioengineering*, 34, 1063–1074 (1989).

*Primary Examiner*—Herbert J. Lilling
*Attorney, Agent, or Firm*—Merchant, Gould, Smith, Edell, Welter & Schmidt

[57] ABSTRACT

The invention provides a method for the direct biological production of calcium magnesium acetate using a novel combination of an aerobic thermophilic bacterium of the genus Bacillus, capable of supporting the sustained production of substantial quantities of acetic acid at low pH, high temperatures, and high salt concentrations. Strains of bacterium of the genus Bacillus selected and isolated for use in the present invention produce acetic acid in the presence of a neutralizing source of calcium and magnesium ions, such as dolomitic lime, to produce substantial quantities of calcium magnesium acetate.

11 Claims, 4 Drawing Sheets

DIRECT CALCIUM MAGNESIUM ACETATE PRODUCTION

GOVERNMENT SUPPORT

This invention was made with government support under contract No. 89034193-4249 by the U.S. Department of Agriculture. The government has certain rights in the invention.

This is a continuation of application Ser. No. 07/699,997, filed May 13, 1991, now abandoned.

TECHNICAL FIELD

The present invention relates to the production of calcium magnesium acetate, and particularly to the direct production of calcium magnesium acetate using thermophilic bacteria of the genus Bacillus.

BACKGROUND OF THE INVENTION

The importance in the world marketplace for the bulk chemical calcium magnesium acetate ("CMA") has been dramatically increasing.

One important use for CMA is as an organic, biodegradable, non-corrosive deicing salt, suitable to replace rock salt (sodium chloride) as the predominate road deicing salt. Each year, millions of tons of sodium chloride and calcium chloride are used for deicing highways. Agoos, A., *Chemical Week*, 144.5, 18–19, (1989); and Marynowski, C. W., J. L. Jones, D. Tuse, and R. L. Broughton, *I&EC Product Res. Devel.*, 24, 457–465, (1985). Sodium chloride is used almost universally because of its excellent deicing properties, wide spread availability, and low delivered costs. Because of its higher costs, calcium chloride is only used when required for effective deicing at lower temperatures.

However, despite its advantages, the costs to society caused by the use of rock salt are enormous. For example, the cost of corrosion to bridges and automobiles, and the contamination of ground water, have been estimated to be nearly fifty times the delivered cost of sodium chloride. Hudson, L. R., Presentation at IGT Conference "Energy from Biomass Waste XI," Mar. 18, 1987. Unfortunately, the cost of currently available alternate, nonpolluting and noncorrosive, deicing materials and methods are too high to attract widespread commercial use.

To address the corrosion problems with rock salt, several corrosion inhibitors are commercially available, such as Cargill's CG-90 ® and Great Salt Lake Mineral and Chemicals' Freezgard ® and Qwiksalt ®. These products, which use phosphate or lignin based corrosion inhibitors, are as effective as salt for deicing, and reduce corrosion. Unfortunately, they do nothing to eliminate the pollution problem posed by the use of salt. The phosphate based inhibitors may, in fact, increase pollution by the addition of phosphate to the highway runoff.

One of the most promising alternate deicing materials is CMA, a mixture of calcium and magnesium acetate, with a Ca/Mg ratio typically between about 1 and 0.5. Dunn, S. A., and R. U. Schenk, *Federal Highway Administration Report FHWA/RD-79/*108, Washington, D.C, 1980. Acetate compounds are attractive replacements because they are nontoxic, noncorrosive to metals, and substantially as effective as rock salt. Calcium and magnesium ions provide improved performance of the mixture over use of the individual ions, and are readily available in high magnesium dolomitic lime and limestone. CMA has been successfully tested in extensive studies in the northern United States and Canada.

A second important use for CMA is as an additive to coal-fired combustion units, such as those used by the electric utilities. In such a use, the CMA acts as a catalyst to facilitate combustion, resulting in more coal being burned for a given size unit. Also, the CMA acts to remove the sulfur in the coal by reacting with the sulfur to form solid calcium sulfate, which is recoverable from the stack gases. Thus, the use of CMA in this manner reduces the serious problem of acid rain. Wise, D. L., Y. A. Levendis, and M. Metahalic (eds.), *Calcium Magnesium Acetate*, Amsterdam: Elsevier Science Publishers, (1991).

These and other important uses for CMA have made it a potentially major industrial chemical. Unfortunately, current commercial methods of producing CMA make it too expensive to be commercially feasible for most applications. Currently, CMA is commercially available, believed to be produced from glacial acetic acid derived from petroleum. The estimated cost of commercially available CMA is approximately twenty times that of rock salt (sodium chloride). Present commercial manufacturing techniques for CMA include combining acetic acid, derived, for example, from petroleum, with calcium and magnesium, for example, from high magnesium dolomitic limestone. However, the cost of separately producing, distilling, and purifying acetic acid, and subsequently reacting it with a calcium and magnesium ion source to form CMA, results in the present high price of commercially-available CMA.

In addition to petroleum sources, acetic acid has been produced through several biological routes. Ghose, T. K. and A. Bhadra, M. Moo-Yung (ed.), *Comprehensive Biotechnology*, 3, 710–729 (1985). Anaerobic bacteria have been studied extensively because of the high theoretical yield. Anaerobic bacteria used to convert inexpensive carbohydrates from starch or cellulosic materials (e.g., glucose or xylose) to acetic acid, include strains of *Clostridium thermoaceticum*, *C. thermocellum*, *C. thermoautotrophicum*, *Acetogenium kivui* or *Acetobacter aceti*. See, e.g., Toda, K., Y. S. Park, T. Asakura, C. Y. Cheng and H. Ohtake, *Appl. Microbiol. Biotechnol.*, 30, 559–563, (1989); Ljungdahl, L. G., L. H. Carreira, R. J. Garrison, N. E. Rabek, L. F. Gunter and J. Wiegle, *U.S. Department of Transportation, Fed. Highway Adm. Rept. FHWA/RD-86/*117, Washington, D.C., (1986); and Lynd, L. R., H. E. Grethlein, and R. H. Wolkin, *Appl. Environ. Microbiol.*, 55, 3131–3139, (1989). However, recovery of dilute acetic acid by distillation of the fermentation broths is extremely energy demanding, and therefore expensive.

Some anaerobic organisms produce acetic acid by the homofermentative pathways which produce three moles of acetic acid from one mole of glucose with no loss of carbon by carbon dioxide. In contrast, acetic acid producing aerobic organisms, such as certain strains of Bacillus, produce only two moles of acetic acid from one mole of glucose. The two-thirds yield for aerobic organisms in producing acetic acid has, prior to this invention, made the commercial production of acetic acid by aerobic organisms to be considered economically impractical, especially when coupled with the extremely expensive recovery by distillation. Ghose, T. K. and A. Bhadra, M. Moo-Yung (ed.), *Comprehensive Biotechnology*, 3, 710–729 (1985).

While the use of aerobic bacteria to produce acetic acid has previously been considered not to be economically feasible, aerobic bacteria of the genus Bacillus are currently used industrially. Bacillus are used in the production of industrial enzymes, such as amylases used to modify starch in the brewing, printing, fabric, or food industries; the production of proteases, used in laundry detergents; and in the production of glucose isomerase, used in the commercial isomerization of glucose to high fructose corn syrups. Many of these industrial processes have used mesophilic Bacillus. High temperature Bacillus species have also been used for the production and identification of thermostable proteins.

Accordingly, there is a need for a direct method of producing CMA at a cost that would make it feasible to use it in a wide range of commercial applications, such as, to replace rock salt as the primary highway deicer. There is also a need for a unique high temperature Bacillus species capable of the sustained production of substantial quantities of acetic acid at low pH and at high salt concentrations.

Accordingly, the present invention provides a method for the direct biological production of calcium magnesium acetate using a novel combination of an aerobic thermophilic bacterium of the genus Bacillus, capable of sustained production of substantial quantities of acetic acid at low pH, and high salt concentrations. The rapid, sustained production of acetic acid, is carried out in the method of the present invention in the presence of a neutralizing source of calcium and magnesium ions, such as dolomitic lime at a pH sufficiently low to dissolve the dolomitic lime, or other neutralizing source of calcium and magnesium ions.

SUMMARY OF THE INVENTION

We have discovered a method of directly producing calcium magnesium acetate (CMA), comprising rapidly growing a high temperature aerobic bacterium of the genus Bacillus, in an aqueous nutrient broth in the presence of an effective amount of a growth substrate, and an amount of a neutralizing calcium and magnesium source sufficient to maintain the pH of the fermentation broth at about 4 to 6.5 and to sustain production of substantial amounts of acetic acid. The acetic acid produced by the Bacillus complexes with available calcium and magnesium ions to form calcium magnesium acetate in the same broth in which the bacteria are grown, and the acetic acid is produced.

Preferably, the growth substrate is a carbon source, such as, hexose sugars, pentose sugars, or mixtures thereof, for example, glucose or xylose. The neutralizing calcium and magnesium source is preferably calcium and magnesium hydroxide or calcium and magnesium carbonate, derived from, for example, crushed high magnesium limestone or dolomitic lime.

Preferably, the neutralizing source of $Ca^{++}$ and $Mg^{++}$ maintains the pH of the fermentation broth at about pH 5 to 6. The temperature of the fermentation broth is typically about 40° to 85° C., preferably about 50° to 65° C. The sustained, rapid growth of the Bacillus is preferably at a doubling time of about 30 to 120 minutes, more preferably 40 to 70 minutes. Such a rate may be achieved where the growth substrate is, for example, glucose. The acetic acid is typically produced at a final yield of about 1 to 50 g/l, and preferably about 5 to 50 g/l. The total concentration of $Ca^{++}$ and $Mg^{++}$ in the fermentation broth is typically about 50 to 500 mM, and preferably about 70 to 250 mM.

The preferred Bacillus species may include *Bacillus stearothermophilus; Bacillus coagulans;* and *Bacillus acidocaldarius,* and *Bacillus* strain A1, and C4, the isolation and characterization of which are described herein, and which are to be deposited with ATCC.

Preferably, only acetic acid is produced rather than mixtures including other acids, such as lactic acid or formic acid.

Other features and advantages of the invention will be apparent from the following detailed description and dependent claims.

DETAILED DESCRIPTION OF THE INVENTION

The present invention provides a novel method for the production of calcium magnesium acetate (CMA), in an economical manner, through a direct biological route. The present method allows for the sustained production of substantial quantities of acetic acid, that is complexed with calcium and magnesium ions, in a single fermentation broth. The method of the present invention avoids the expense of the energy intensive recovery of concentrated acetic acid, whether from petroleum sources, or from dilute aqueous fermentation media. Previously, after concentrated acetic acid was recovered it was subsequently reacted with a calcium and magnesium ion source, to form CMA.

The present invention provides a direct method of production of CMA that can produce acetic acid at a rapid, sustained rate, at a low pH, and at a high temperature. The thermophilic organisms used in the present method have a high magnesium and calcium tolerance, minimal side product formation, other than carbon dioxide. Because of the low pH, high salt, and high temperature of the method of the present invention, it is unlikely that sterilized media will be required. The high temperature of the present invention has the additional advantage of requiring less heat to evaporate the final CMA product.

The unique method of the present invention, directly produces CMA in a single fermentation broth, combines unique aerobic thermophillic organisms capable of sustaining production of acetic acid even at low pH, with the tolerance to the high salt concentrations caused by the dissolved neutralizing calcium and magnesium source (e.g., dolime). In addition, the method of the present invention preferably provides an organism that sustains production of only acetic acid, and does not make additional contaminating acids such as lactic or formic acid. This novel combination allows CMA to be produced at a low cost.

GROWTH SUBSTRATE

The method of the present invention requires providing an aqueous fermentation broth suitable to support the growth of the strain of Bacillus utilized. The fermentation broth will include a suitable growth substrate in a concentration effective to support and sustain growth at the desired rate. The desired final concentration of acetic acid production may vary, but a final concentration of about 1 to 50 g/l would typically be expected, with about 5 to 50 g/l preferred. Because reducing the cost of the production of CMA is important, inexpensive growth substrates, such as those from waste materials, are preferred.

Substrates capable for supporting growth of thermophilic bacteria of the genus Bacillus, include hexose sugars, pentose sugars, and mixtures thereof, such as, glucose, sucrose, xylose, or lactose. Starch is a suitable source for glucose, and may come from, for example, corn starch, or starch from cassava or tapioca. Pentose sugars are easily obtained from agricultural and wood wastes by dilute acid hydrolysis at 60° C. Wilson, J. J., L. Deschatelets, and N. K. Nishikawa, *Appl. Microb. Biotechnol.*, 31, 592–596, (1989). Waste from food processing, agriculture (e.g. corn cobs or corn stover), or the paper industry, may provide a suitable inexpensive source of a growth supporting substrate. Xylose is the major component of hemicellulose, a component of corn stover, bagasse, seed hulls, wood chips, wheat straw, rice straw, and peanut shells. Cellulose is also useful, and is available from plentiful and inexpensive sources. Lactose from cheese whey is also considered a potentially useful waste, and is an inexpensive source of dilute carbohydrate.

NEUTRALIZING CALCIUM AND MAGNESIUM SOURCE

The source of calcium and magnesium utilized in the present invention serves at least two functions. First, the calcium and magnesium ions provided in the fermentation broth complex with the acetic acid that is produced by the Bacillus to form the desired calcium magnesium acetate. Secondly, it is difficult to sustain the production of an acid by a bacterium in a broth that becomes too acidic. As the pH drops, normally, an organism will halt production of acid products at a given point. Therefore, the calcium and magnesium source should also buffer the pH of the fermentation broth, so that the pH stays in a desired range throughout the process, and acetic acid continues to be produced in substantial quantities. The neutralizing calcium and magnesium source can be added to the fermentation broth at a rate that maintains the pH in the desired range.

The use of the calcium and magnesium source provides an additional constraint for the organism used to produce the acetic acid; the requirement for high salt tolerance. For example, acetic acid producing bacteria of the genus Clostridium are not capable of growing under such high salt conditions.

Crushed dolomitic high magnesium limestone, or dolime, produced from dolomitic sources, are inexpensive and abundant neutralizing agents that provide the require calcium and magnesium ions. Dolomitic limestone typically contains about 40–44% magnesium carbonate, and 54–58% calcium carbonate. Boynton, R. S., *Chemistry and Technology of Lime and Limestone* 2nd. Ed., (1980). In the neutralization reaction it provides calcium and magnesium ions at the appropriate ratio (approximately 1 to 1) for good deicing performance of the resulting CMA. Dunn, S. A. and R. U. Schenk, *Federal Highway Administration Report FHWA/RD-79/108*, Washington, D.C., (1980). Crushed limestone typically has an equilibrium pH of about 4.5. However, the dissolution rate may be slower than that preferred to support rapid growth of certain strains of Bacillus, and to neutralize, and sustain, rapid production of acetic acid, and CMA.

Dolime is made from crushed dolomitic limestone. Dolime is made by partially rehydrating the crushed, baked limestone to provide a source for calcium and magnesium hydroxide (40–44% magnesium hydroxide, 54–58% calcium hydroxide). Dolime can be added to the broth at a desired rate, and dissolved to provide a fermentation broth with a pH that can be controlled in the range of about 5 to 6. Thus, for a rapid acid producing organism, dolime is preferred over crushed limestone.

The preferred upper limit for the pH of the fermentation broth is about 6.5, because dolime, a preferred neutralizing source of calcium and magnesium, is increasingly difficult to dissolve at a pH above about 6.5. The preferred pH range for the method of the present invention is about 4 to 6.5, with a pH of about 5 to 6 being more preferred.

TEMPERATURE

The preferred temperature range for the method of the present invention is about 40° to 85° C., with about 50° to 65° C. being most preferred. These high temperatures are advantageous because the high temperatures also aid in the gelatinization of starch as well as providing an environment in which most mesophilic bacteria that could potentially contaminate the process would not be able to grow.

BACILLI

The present invention utilizes aerobic fermentation to directly produce substantial quantities of acetic acid in the presence of a neutralizing source of calcium and magnesium, such as dolime or crushed limestone.

Bacillus useful in the present invention may include strains of *B. stearothermophilus, B. acidocaldarius,* and *B. coagulans.* The strains A1 (ATCC #55187) and C4(ATCC #55182), isolated and characterized, as described in the Examples, are also preferred.

The utilization of aerobic fermentation to directly produce acetic acid in the presence of dolime or crushed limestone eliminates the energy-intensive azeotrophic distillation method of recovery required to concentrate acetic acid from dilute aqueous fermentation media prior to formation of CMA by a subsequent reaction with, for example, dolomitic lime, in a separate vessel.

Strains of *Bacillus stearothermophilus,* a thermophilic Bacilli, are well suited for acetate production from a variety of carbohydrate sources, including xylans, pentoses, starches and glucose. These Bacillus may grow at acid pH, and can be adapted to tolerate high levels of $Mg^{++}$ and $Ca^{++}$ ions. The Bacillus may be selected, or genetically engineered, to aerobically ferment glucose and xylose to acetic acid. Even though the theoretical yield of this proposed route is limited to 66% of the carbon due to the aerobic fermentation, the thermophilic Bacilli are attractive due to their rapid growth, salt tolerance, and established use in industry (albeit, for different end products), and the ability to inoculate with spores.

An interesting feature of spore-forming Bacillus is their ability to accumulate acetate during vegetative growth and then metabolize it during sporulation. Hanson, R. S., V. R. Srinivasan, and H. O. Halvorson, *J. Bacteriol.*, 85, 451–460, (1963). The mechanism for this process was discovered by work on the regulation of the TCA cycle. See, e.g., Hanson, R. S., J. Blicharska, and J. Szulmajster, *Biochem. Biophys. Res. Comm.*, 17, 1–7, (1964); Hanson, R. S., and D. P. Cox, *J. Bacteriol.*, 93, 1777–1787, (1967). Investigators have speculated that the accumulated acetic acid can be increased by manipulating the activity of the key enzyme citrate synthase. Fukaya, M., H. Takemura, H. Okumura, Y. Kawamura, S. Horinuchi, and T. Beppa, *J. Bacteriol.*, 170, 2096–2104, (1990). A genetic engineering approach to the manipulation of the citrate synthase enzyme is being suggested by Schendel et al. as reported in Schendel. F. J., P. R. August, C. R. Anderson, R. S. Hanson, M. C. Flickinger, "Cloning and Nucleotide Sequence of the Gene Coding for Citrate Synthase from a Thermotolerant Bacillus sp.," in press, (1991). The citrate synthase gene has been identified and sequenced in order to investigate its regulation and activity.

It is believed that the means of growing Bacillus having the claimed characteristics of the instant invention, including substantial and sustained production of acetic acid that can complex to form CMA, is enhanced through manipulation of the enzyme citrate synthase. Mutants lacking citrate synthase will produce acetic acid in high yield because of the inability to metabolize acetyl-CoA. Carbon sources will be converted only to acetate if glutamate is supplied to the organisms to support growth in the absence of citrate synthase. Therefore, mutation or alteration of the disclosed and claimed Bacillus species, to regulate the activity of a citrate synthase enzyme, could be used to exhibit enhanced sustained production of acetic acid, by means of the methods taught by the instant invention.

The desired characteristics of an acetate over-producing Bacillus suitable for use in the methods of the present invention include: secretion of only acetic acid (not a mixture of organic acids) from metabolism of glucose or pentose sugars; inability to utilize accumulated acetate (accomplished by mutation or alteration of the bacilli strain to regulate citrate synthase expression); expression of a thermostable amylase to solubilize and hydrolyze starch; growth at thermophilic temperatures (preferably 50°–65° C.) to make CMA evaporation more efficient (FIGS. 1,2); tolerance to high levels of acetic acid (up to 50 g/l) at pH 4–6.5; sustained and rapid growth and acetic acid production where pH is maintained at pH 5–6; tolerance to high levels (70–250 mM) of $Ca^{++}$ and $Mg^{++}$ ions, particularly when using dolime for neutralization.

The fermentation process (e.g., FIGS. 1 and 2) may be carried out in an efficient large scale reactor, such as a plug flow reactor to maximize the transfer of oxygen, and to minimize the effects of product inhibition. The pH can be controlled at pH 5–6 during the fermentation by the continuous addition of the neutralizing agent (e.g., dolime) at a controlled rate, neutralizing the acetic acid as it is produced to minimize inhibition due to acetic acid accumulation. At the completion of the fermentation, the pH is preferably adjusted to about pH 9 to precipitate residual extracellular proteins, and CMA can be concentrated by multiple effect evaporation (FIGS. 1 and 2).

TYPICAL PROCESS STEPS

Figure 1:
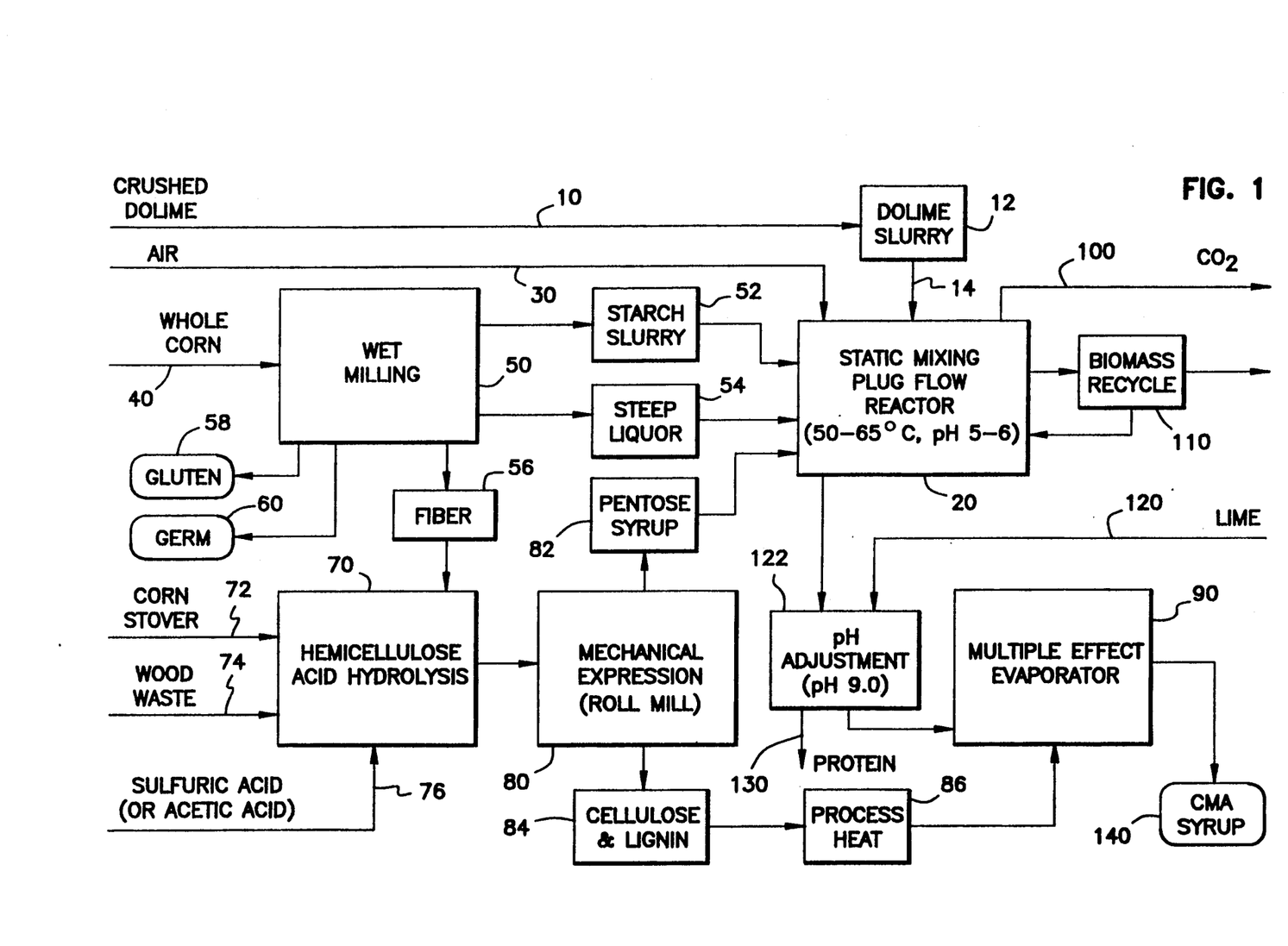
FIG. 1 is a process diagram for the direct production of CMA from whole corn or hemicellulosic wastes.
Figure 2:
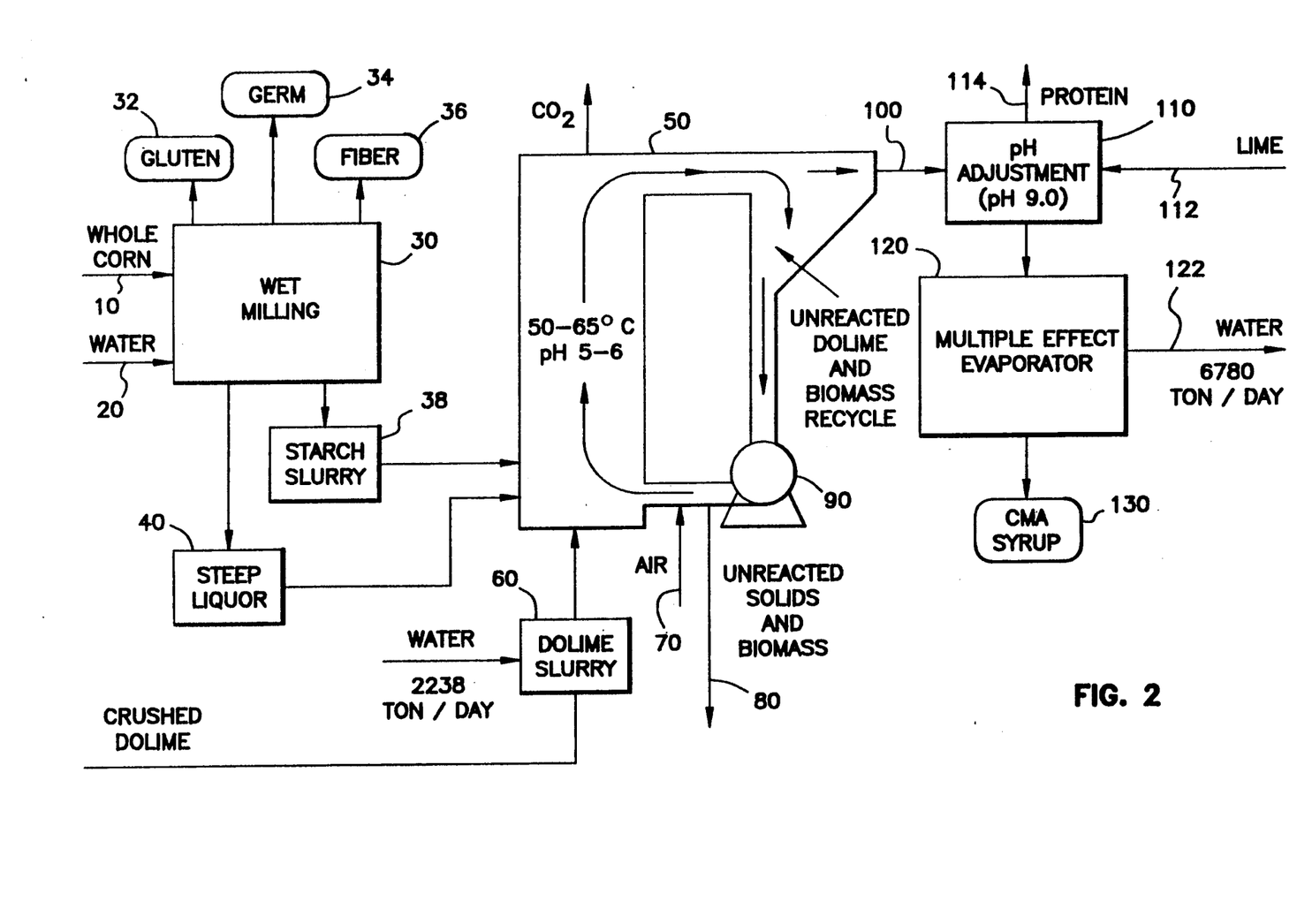
FIG. 2 is a process diagram for the production of CMA from whole corn using a plug flow reactor.

Referring to FIG. 1, a process diagram for CMA production from whole corn or hemicellulosic wastes is shown. The reactants include crushed dolime, air, whole corn, corn stover, wood waste, and sulfuric acid. Crushed dolime is fed through a feed line 10, into a dolime slurry 12, that feeds through a feed line 14 into the plug flow reactor 20. The plug flow reactor is at a temperature of 50°–65° C. and a pH of 5–6. Air is fed into the plug flow reactor through a feed line 30.

Whole corn is fed through a feed line 40 into a wet milling vessel 50. From the wet milling vessel 50, a starch slurry 52, steep liquor 54, fiber 56, gluten 58 and germ 60 are separated and removed from the wet milling vessel 50. The fiber 56 is fed into a hemicellulose acid hydrolysis vessel through which corn stover is fed through a feed line 72, wood waste through a feed line 74 and sulfuric acid through a feed line 76. The contents of the hemicellulose acid hydrolysis vessel 70 are fed into a mechanical expression roll mill 80 that separates the pentose syrup 82 from the cellulose and lignin 84. Cellulose and lignin can be combusted to produce process heat 86 used to drive a multiple effect evaporator 90. The starch slurry 52, the steep liquor 54 and the pentose syrup 82 are also fed into the plug flow reactor 20 for reaction with the dolime slurry 12, and the air. Carbon dioxide is given off and moved through a carbon dioxide exhaust line 100. Biomass is recycled through a biomass recycling vessel 110. After suitable reaction in the plug flow reactor 20, the fermentation broth is pH adjusted to pH 9 in pH adjustment vessel 122, through the addition of additional lime through feed line 120. Protein is precipitated off through protein exit line 130. The contents of the pH adjustment vessel 122 is fed into the multiple evaporator 90 and is heated at least in part through process heat 86. After evaporation, CMA syrup is collected in a CMA syrup collection vessel 140.

Turning to FIG. 2, a second process diagram for CMA production for whole corn using a plug flow reactor is shown. Whole corn 10 and water 20 are fed into a wet milling vessel 30. Gluten 32, germ 34, fiber 36 and a starch slurry 38 and a steep liquor 40 are separated from the wet milling vessel 30. The steep liquor 40 and the starch slurry 38 are fed into the plug flow reactor 50. A dolime slurry 60 is also fed into the plug flow reactor 50 along with an air source 70. Unreacted solids in biomass 80 are removed from the plug flow reactor 50. Unreacted dolime and biomass are recycled through a biomass recycler 90. The contents of the plug flow reactor 50 exit through a CMA slurry exhaust conduit 100 into a pH adjustment vessel 110. Lime 112 is added to the pH adjustment vessel 110 to adjust the pH to 9. Protein 114 is precipitated from the pH adjustment vessel 110 and the remaining contents are deposited in a multiple effect evaporator 120. Water 122 and CMA syrup 130 are produced by the multiple effect evaporator 120.

CMA PRODUCT

The CMA broth can be concentrated to a CMA concentration of about 30%, or any other concentration desired for a given end use. A 30% CMA syrup can be mixed directly with sand and applied to deice a roadway. In the production of electrical power from coal, CMA syrup may be sprayed directly onto coal and combusted to reduce sulfur pollution.

The invention will be further described by reference to the following detailed Examples.

EXAMPLE 1

Isolation and characterization of bacteria of the genus Bacillus suitable for production of acetic acid at low pH and high salt Media for plate counts, shake flask studies, 3 liter fermentations, and the inoculum cultures were generated by adding together various concentrated premixes. The premixes used in the instant Examples were: 1) a minimal salt solution, 2M $(NO_3)_2$, 2M $MgSO_4$; 2) 10% yeast extract (Difco Laboratories, Detroit, Mich.; 3) 50% glucose; 4) 50% D-Xylose; 5) 10% oil mixture consisting of equal amounts of burning lard (George Pfau, Eddyville, Ind.), herring (H. J. Baker, New York, N.Y.), and corn oil (Cargill, Eddyville, Ind.); 6) 300 g/l glutamic acid neutralized to pH 7 with NaOH; and 7) chloride-free trace salts. Each of these solutions, except for the trace salts, was autoclaved for one-half hour. The minimal salt solution for dilution plating, cell washing, and shake flasks experiments included the appropriate amount of $K_2HPO_4$, $KH_2PO_4$, and $(NH_4)_2SO_4$ autoclaved for one-half to one hour depending on the volume of solution. The ratio of $K_2HPO_4$ to $KH_2PO_4$ was set so that the pH of the finished media was at the desired level between pH 5.0 and 5.5. The final pH was then adjusted by adding concentrated $H_2SO_4$ or NaOH. For 3 liter fermentations, the appropriate amount of yeast extract was added to the minimal salt solution before autoclaving.

Neutralizing calcium and magnesium sources were added to the fermentor by a peristaltic pump. The neutralizing calcium and magnesium sources included 0.5M NaOH, 4% dolime (Mircle Lime, pressure hydrated type "S", Western Lime and Cement, 40–44% magnesium hydroxide, 54–58% calcium hydroxide, equivalent to 0.11N NaOH), and 4% crushed limestone (Corson 200 Mesh Pulverized Limestone, Plymouth Meeting, Pa.). These solutions were autoclaved for one-half hour. Defoamer when needed was added manually to the fermentor as an autoclaved 10% water emulsion of Dow Corning AF.

The organisms were isolated by the following method. Approximately 200 soil samples were screened for organisms capable of using xylose at 50° C. Five percent water suspensions of each soil sample were pretreated at 80° C. to kill vegetative cells. The samples were plated on xylose/dolime media and grown overnight at 50° C. Colonies were picked and streaked on xylose./dolime media to isolate single cells. Of the over 300 organisms isolated, 25 also grew in minimal media containing xylose, 100 mM $CaCl_2$, and 100 mM $MgCl_2$ at pH 4.0. Single colonies were streaked onto xylose/dolime slants containing a pH indicator. Those colonies showing acid production were further tested by culturing in shake flasks using minimal media containing xylose followed by analysis of the culture fluids by HPLC to determine the production of acetic acid. Acid-tolerant, acetic acid producing colonies were selected. Shake flask studies were conducted to monitor absorbance and pH changes during growth on media containing added acetate and dolime. Also a rapid screening method was established to access growth and acid production as a function of media pH. From this work, two organisms designated as strains A1 and C4 were selected.

Characterization of the selected organisms was conducted. Characterization studies showed A1 and C4 to be closely related to *Bacillus coagulans*.

Initially strains A1 and C4 were stored on plates at 4° C. Spores were prepared and used to start inocula for three liter batch fermentations. Spores were prepared by growing cells in 200 ml of pH 5.5 (adjusted) media containing 8 g/l nutrient broth (Difco) and 5 g/l D-xylose at 55° C. in shake flasks for 8 hours until a dense culture was obtained, and then shifting the temperature to 24° C. Sporulation metals consisting of 0.2M $MgCl_2$, 0.14M $CaCl_2$ and 0.01M $Mn_2Cl$ were then added at a concentration of 5 ml/l and the culture was shaken at 24° C. overnight. The crude mixture of vegetative cells and spores were centrifuged and resuspended in 10 ml of water. Spores were stored frozen at $-10°$ C. in water.

EXAMPLE 2

Analysis

Acetate was determined by HPLC using a $7.8 \times 300$ mm BioRad HPX-87H column in a liquid chromatograph with a variable wavelength detector set at 210 nm. The analysis was run in the isocratic mode using a 10 microliter injection, 0.8 mM $H_2SO_4$ as the eluent (at 0.6 ml/min) and a temperature of 50° C. Samples of centrifuged fermentation broth were prepared by dilution with an equal volume of 130 mM $H_2SO_4$ and centrifuged again. The acetate peak area (eluted at 13.7 minute) was integrated and compared to standard samples. Carbohydrates (glucose or xylose) were determined by HPLC using a $7.8 \times 300$ mm BioRad HPX-87C column with BioRad Guard cartridges (Model #125-0118), a refractive index detector and integrator. Samples were run in an isocratic mode with an injection volume of 10 microliters of centrifuged fermentation broth, and flow rate of 0.6 ml per minute at 65° C. The xylose peak eluted at 6.5 minutes and the glucose peak at 7.5 minutes. The peaks were quantitated by peak area and compared to standard samples.

Dissolved oxygen in the 3 liter fermentor was measured using a galvanic dissolved oxygen probe with a 2 mil Teflon membrane Borkoski, J. D., and M. J. Johnson, *Biotechnol. Bioeng.*, 9, 635–639, (1967).

Optical density measurements for monitoring cell growth were determined using a spectrophotometer at 600 nm.

Viable cell number was determined by a dilution spread plate procedure as outlined by Koch, A. L., P. Gerhardt, *Manual of Methods for General Bacteriology*, American Society for Microbiology, Washington, D.C. 179–207 (1981). The dilutions were $10^{-2}$, $10^{-4}$, $10^{-5}$, $10^{-6}$, and $10^{-7}$. A 0.1 ml sample was spread on each plate. Special care was taken to match the agar composition and the diluent solution to the media composition, and pH. In addition, the diluent temperature was controlled at 55° C. to avoid temperature shock. The plates were incubated at 55° C. for 24 hours. The plates were manually counted.

EXAMPLE 3

Dissolution/neutralization of limestone

Figure 3:
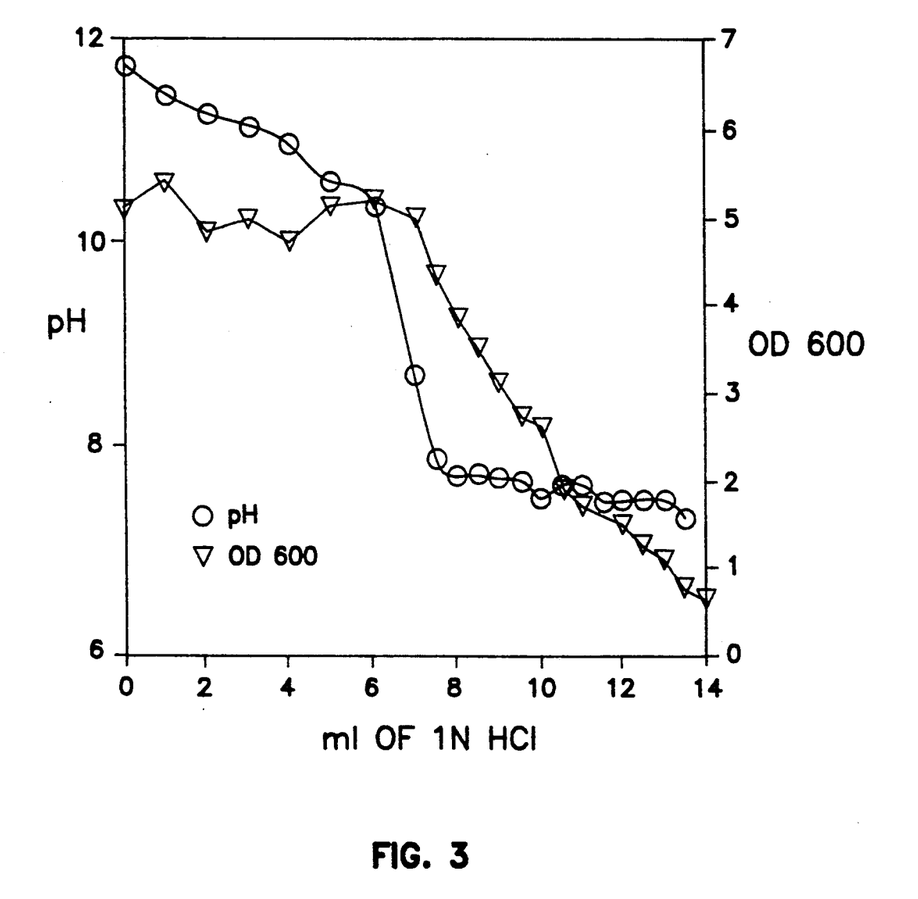
FIG. 3 is a titration curve for 4% dolime plotting pH and the degree of turbidity measured at 600 nm (y-axis) against ml of 1N HCl (x-axis)

In the process of the present invention, a neutralizing magnesium and calcium source can be added to the process by an initial charge of crushed limestone. The limestone remains insoluble until acid is formed and reacts with it in a neutralization reaction. The characteristics of limestone neutralization were determined by an experiment using the 3 liter fermentor as a neutralizing reactor. Glacial acetic acid was metered into the reactor to react with an initial charge of limestone suspended in water. This process was monitored by observing the pH as glacial acetic acid was slowly added to the reactor at a controlled rate. The pH of the solution was monitored until a steady state was reached. The results are reported in FIG. 3.

EXAMPLE 4

Fermentation of strain C4 to produce acetic acid and CMA

Strain C4 isolated and characterized as described in Example 1, was grown in a fermentation broth to produce acetic acid and CMA. Growth was rapid with acetate accumulation both during rapid growth and following cessation of growth.

Carbohydrate type (glucose or D-xylose) and concentration (2.5 to 40.0 g/l), yeast extract level (0.25 to 6 g/l), buffer level (30 120, and 240 mM phosphate), neutralizing agent (NaOH, dolime and limestone), glutamate level (0–1.5 g./l), and pH control point (4.9–6.0) were varied during the study. Fermentation temperature (53° C.), nitrogen level (30 mM $(NH_4)_2SO_4$), calcium ion concentration (30 mM), and Mg ion concentration (30 mM) were held constant throughout the study. In two experiments, glucose was batch-fed into the fermentation; in another limestone (as a neutralizing agent) was added at the beginning of the run.

Figure 4:
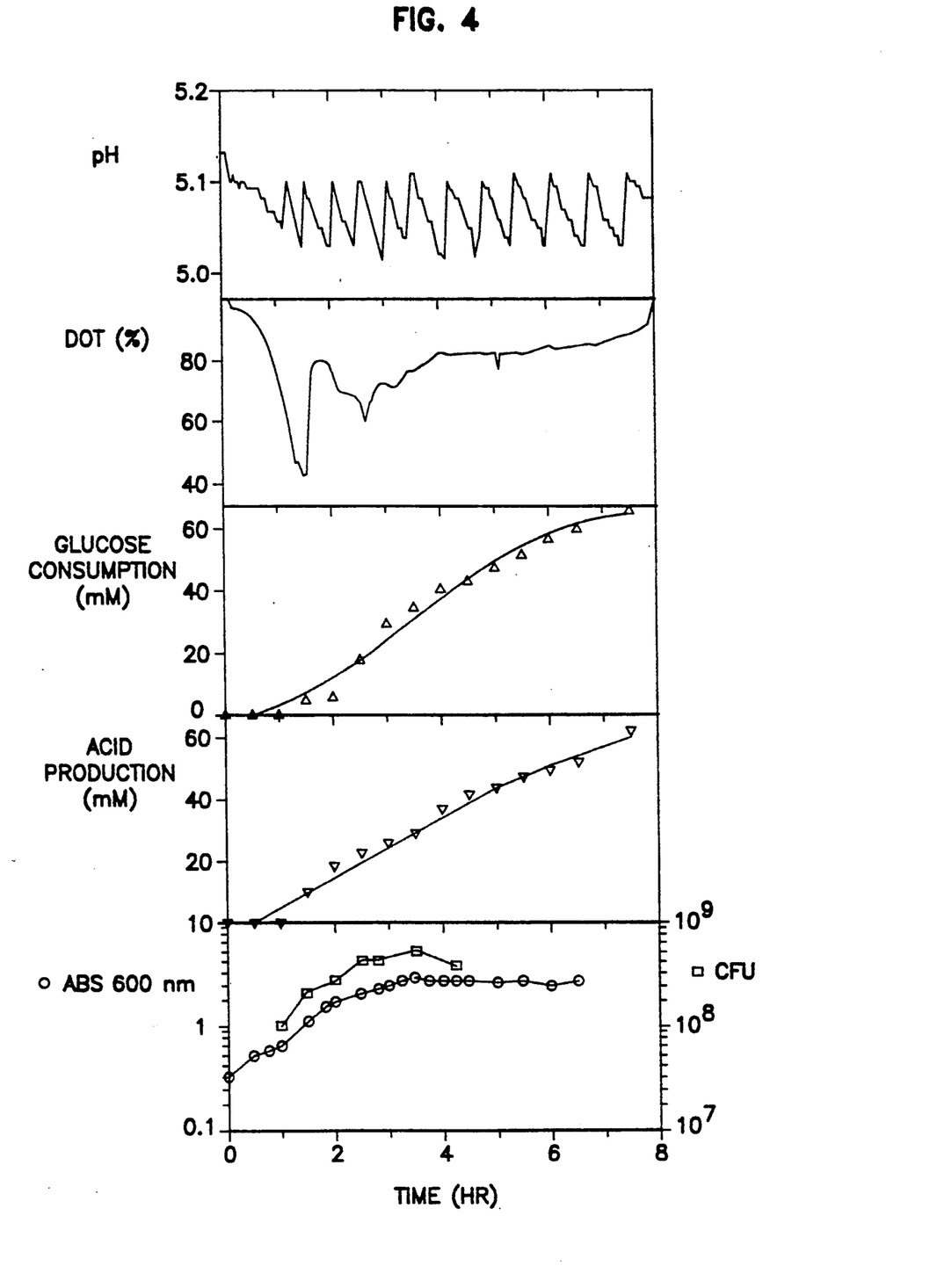
FIG. 4 is a plot showing absorbance at 600 nm; acid production (mM); glucose consumption (mM); dissolved oxygen (%); and pH on the y-axis versus time in hours on the x-axis.

FIG. 4 shows pH, dissolved oxygen, the yield of acetic acid based on the acetate produced, the glucose consumed during fermentation, and a growth curve.

Production of acetate was rapid, and both during growth and non-growth periods. Fermentation runs were 4.0 to 9.5 hours in duration. Sampling was terminated after the stationary phase was reached and the production of acetic acid (measured by base addition) stopped.

TABLE 1

Composition of Chloride-Free Concentrated Trace Metals Stock Solution

| | |
|---|---|
| 2.0 g/l | $FeSO_4.7H_2O$ |
| 0.04 g/l | $CuSO_4.5H_2O$ |
| 0.03 g/l | $H_3BO_3$ |
| 0.15 g/l | $MnSO_4.H_2O$ |
| 0.2 g/l | $ZnSO_4.7H_2O$ |
| 0.047 g/l | $Na_2MoO_4.2H_2O$ |
| 0.047 g/l | $CoSO_4.7H_2O$ |

Adjusted to pH 7.0 with $H_2SO_4$, sterile filtered.

We claim:

1. A method of producing calcium magnesium acetate comprising:
   growing under aerobic fermentation conditions a pure strain high temperature acetic acid-producing aerobic bacterium selected from a group consisting of *Bacillus stearothermophilus*, *Bacillus coagulans*, and *Bacillus acidocaldarius*, said aerobic bacterium growing at pH 4.0 and 50° C. with glucose, sucrose, xylose, lactose, monosodium glutamate, or a mixture thereof as a growth substrate in an aqueous fermentation broth having an effective amount of a growth substrate, and an amount of a neutralizing calcium and magnesium source sufficient to maintain the pH of the broth at about 4 to about 6.5 and sustain substantial production of acetic acid; and
   wherein the acetic acid produced by said aerobic bacterium complexes with available calcium and magnesium ions to produce calcium magnesium acetate.

2. The method of claim 1 wherein said aerobic bacterium is *Bacillus stearothermophilus*.

3. The method of claim 1 wherein said aerobic bacterium is *Bacillus coagulans*.

4. The method of claim 1 wherein said aerobic bacterium is *Bacillus acidocaldarius*.

5. The method of claim 1 further including a step of adding a subsequent amount of a neutralizing agent to raise the pH of the fermentation broth to a pH of about 8–10.

6. The method of claim 1 further including a step of transferring said fermentation broth containing CMA to a subsequent evaporation vessel to concentrate said CMA to CMA syrup.

7. A method of producing calcium magnesium acetate comprising:
   growing under aerobic fermentation conditions a pure strain high temperature acetic acid-producing aerobic bacterium selected from a group consisting of Bacillus sp. Al (ATCC No. 55187) and Bacillus sp. C4 (ATCC No. 55182), said aerobic bacterium growing at pH 4.0 and 50° C. with glucose, sucrose, xylose, lactose, monosodium glutamate, or a mixture thereof as a growth substrate in an aqueous fermentation broth having an effective amount of a growth substrate, and an amount of a neutralizing calcium and magnesium source sufficient to maintain the pH of the broth at about 4 to about 6.5 and sustain substantial production of acetic acid; and
   wherein the acetic acid produced by said aerobic bacterium complexes with available calcium and magnesium ions to produce calcium magnesium acetate.

8. The method of claim 7 wherein said aerobic bacterium is Bacillus sp. Al (ATCC No. 55187).

9. The method of claim 7 wherein said aerobic bacterium is Bacillus sp. C4 (ATCC No. 55182).

10. The method of claim 7 further including a step of adding a subsequent amount of a neutralizing agent to raise the pH of the fermentation broth to a pH of about 8–10.

11. The method of claim 7 further including a step of transferring said fermentation broth containing CMA to a subsequent evaporation vessel to concentrate said CMA to CMA syrup.

* * * * *

UNITED STATES PATENT AND TRADEMARK OFFICE
CERTIFICATE OF CORRECTION

PATENT NO. : 5,316,928

DATED : May 31, 1994

INVENTOR(S) : Michael C. Flickinger et al.

It is certified that error appears in the above-identified patent and that said Letters Patent is hereby corrected as shown below:

```
At column 2, line 60, for "Bacillus" read --Bacilli--

At column 3, line 4, for "Bacillus" read --Bacilli--

At column 3, line 11, for "Bacillus" read --Bacilli--

At column 6, line 40, for "Bacillus" read --Bacilli--

At column 6, line 56, for "Bacillus" read --Bacilli--

At column 9, line 17, for "Ind." read --IA--

At column 9, line 18, for "Ind." read --IA--
```

Signed and Sealed this

Fourth Day of June, 1996

*Attest:*

BRUCE LEHMAN

*Attesting Officer*   *Commissioner of Patents and Trademarks*